United States Patent
Zhang et al.

(10) Patent No.: US 12,371,395 B2
(45) Date of Patent: Jul. 29, 2025

(54) BISPHENOL A PREPARATION PROCESS AND DEVICE THEREOF

(71) Applicant: TIANJIN UNIVERSITY, Tianjin (CN)

(72) Inventors: Minhua Zhang, Tianjin (CN); Yingzhe Yu, Tianjin (CN); Hao Gong, Tianjin (CN); He Dong, Tianjin (CN); Feng Shi, Tianjin (CN); Haoxi Jiang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/924,505

(22) Filed: Oct. 23, 2024

(65) Prior Publication Data
US 2025/0197330 A1 Jun. 19, 2025

(30) Foreign Application Priority Data
Dec. 14, 2023 (CN) .......................... 202311716398.4

(51) Int. Cl.
C07C 37/16 (2006.01)
B01J 8/04 (2006.01)
C07C 37/68 (2006.01)

(52) U.S. Cl.
CPC ............ C07C 37/16 (2013.01); C07C 37/685 (2013.01)

(58) Field of Classification Search
CPC ............ C07C 37/16; C07C 37/68; B01J 8/04
See application file for complete search history.

(56) References Cited

U.S. PATENT DOCUMENTS 4,308,404 A 12/1981 Kwantes et al.

FOREIGN PATENT DOCUMENTS

| CN | 1080914 A | 1/1994 |
|---|---|---|
| CN | 1172688 A | 2/1998 |
| CN | 1390819 A | 1/2003 |
| CN | 1616387 A | 5/2005 |
| CN | 115350651 A | 11/2022 |
| CN | 116020353 A | 4/2023 |
| CN | 117384015 A | 1/2024 |
| IN | 2701DELNP2008 A | 7/2008 |
| WO | 2004013075 A1 | 2/2004 |
| WO | 2008100165 A1 | 8/2008 |

OTHER PUBLICATIONS

Bohan Yang, "Practical Introduction of Chemical Safety Production Basic Knowledge" Feb. 2017.
Huisheng Lu et al., "New Stripping Process with Multi-stages Suspended Bed for Production of Bisphenol A", Tianjin R & D Center for Petrochem Technology Tianjin University Dec. 17, 1996.
Jitang Yuan et al. "Study on New Condensation Reactor and Technology in the Production of Bisphenol A", Tianjin R & D Center for Petrochem Technology, Jul. 22, 1993.
Pengfei Zhou et al. "Discussion of Bisphenol—A Producing Methods", Shanghai SINOPEC Mitsui Cemicals Co., Ltd., Feb. 28, 2015.
Zuyuan Xue "Current Situation and Prospect of Bisphenol A Production Process Technology", Tianchen Chemical Engineering Corporation of China, Apr. 30, 2006.

*Primary Examiner* — Sikarl A Witherspoon

(57) ABSTRACT

The present disclosure relates to a bisphenol A preparation process and device thereof. Each stage of reaction system includes a cooler and reactors, each with four sections, the reactors are filled with bisphenol A synthetic resin catalysts before startup operation, and filling proportions of the catalysts are as follows: ⅓ of the catalysts for the first-section reactor, ⅔ for the second-section reactor, the full amount for the third-section reactor and the full amount for the fourth-section reactor. The three reactors operate in series connection through valves, the reactor with the deactivated catalyst is cut out and the reactor to be used is cut in to maintain the three reactors operating in series every time the system operates ⅓ of the service life of the catalyst, and the process can provide a larger air speed, which is beneficial to eliminating the influence of external diffusion, thereby obtaining higher product benefits.

7 Claims, 1 Drawing Sheet

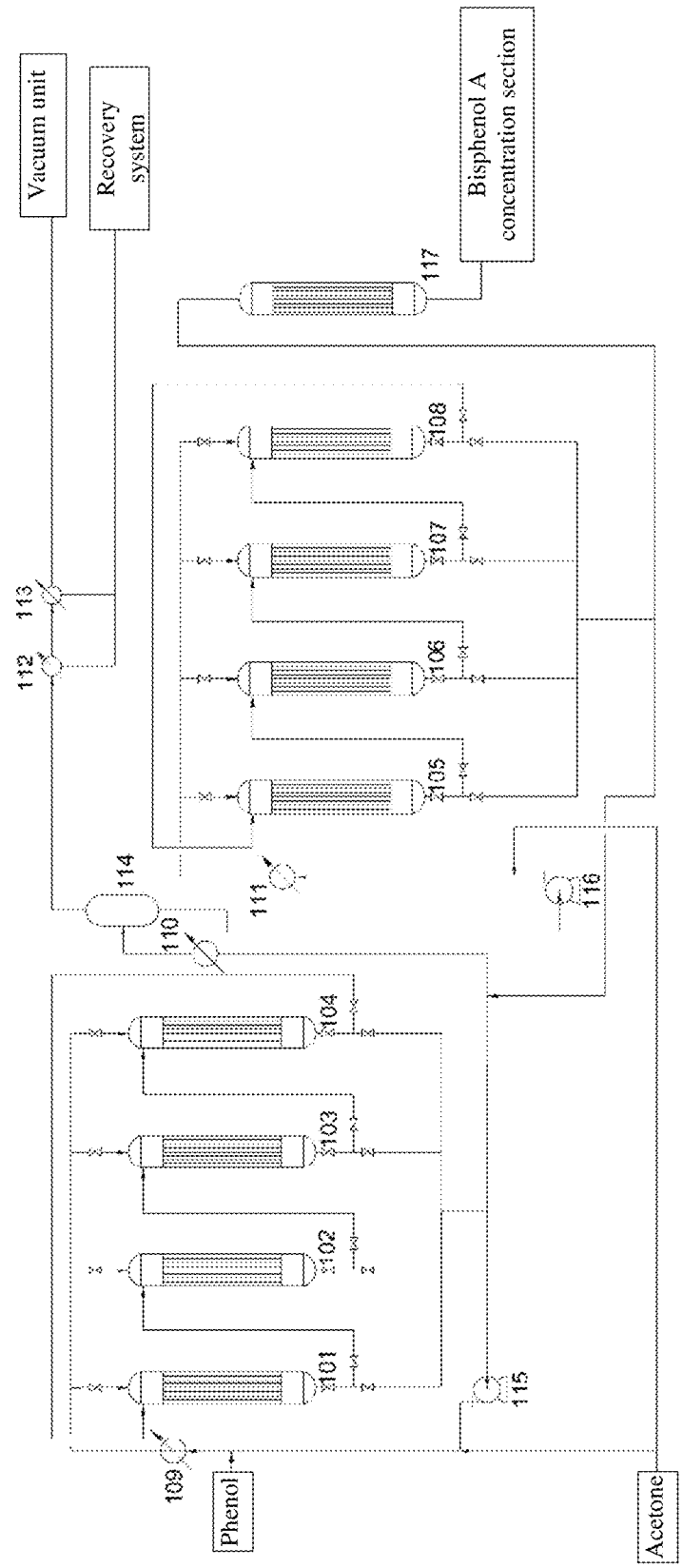

BISPHENOL A PREPARATION PROCESS AND DEVICE THEREOF

CROSS-REFERENCE TO RELATED APPLICATION

This application claims priority from the Chinese patent application 2023117163984 filed Dec. 14, 2023, the content of which is incorporated herein in the entirety by reference.

TECHNICAL FIELD

The present disclosure relates to a bisphenol A preparation process and device thereof, in particular to a technical solution for series operation of reactors and a solution for filling proportions of catalysts in the reactors before startup and trial operation.

BACKGROUND ART

Bisphenol A is produced by acetone and excess phenol through a condensation reaction at an appropriate temperature and pressure and under catalysis, and the reaction is an exothermic reaction with water generated. It was mentioned in Bisphenol A compiled by Mr. Liang Shuxiang that a thermal effect of a condensation reaction between phenol and acetone was 98 kcal/kg. In order to maintain a specified reaction temperature, a circulating heat extraction pump is arranged in each stage of reaction system. Excess phenol materials circulate back to the reaction system to take away part of heat to maintain the reaction at an appropriate temperature. In order to facilitate the reaction and reduce a toxic effect of water on catalysts, it was mentioned in Chiyoda Corporation: Advanced Process for Production of BPA, CT-BISA Process, 1996 from Mitsubishi Chemical Corporation that unreacted acetone, water and phenol in a reaction mixture were fed into three distillation towers for separation, the separated acetone and phenol circulated back to synthesis reactors to continue to participate in the reaction, water was discharged from bottoms of the distillation towers as wastes, however, a method of separating reactants by a plurality of distillation towers one by one would result in a large amount of energy and economic losses. The present disclosure provides an interstage dehydration system which removes wastes generated in a first-stage reaction system at a time in a flash evaporation method,, thereby reducing energy loss while ensuring product quality.

GE Company adopted a single two-layer fixed-bed condensation reactor for the reaction, achieving single-pass conversion rates of approximately 50% for acetone and approximately 10% for phenol respectively (Bisphenol A and Alkylated Phenols, PEP Report, No. 1921988Dec). A total yield of BPA was 91% specific to the phenol, but maximum processing capacity of the single device reactor was approximately 240,000 tons per year, which could not meet a development trend of large-scale industrial production. In order to further improve a reaction conversion rate and selectivity, the present disclosure develops three series-connected fixed-bed reactors featuring circulation, thereby increasing an air speed and reaction driving force so as to obtain a higher conversion rate.

A single fixed-bed reactor or fixed-bed reactors connected in parallel and fully loaded with catalysts are mostly used in the industry for the synthesis of bisphenol A, and the catalysts for the synthesis of the bisphenol A are mainly ion exchange resin. During startup and trial operation of the system, it is necessary to remove all the catalysts in full load and send the catalysts for evaluation analysis in a case that product quality is not up to standard, resulting in waste of a large quantity of manpower and material resources. CN 202111648943.1 has disclosed a method and device for replacing catalysts in a bisphenol A synthesis process. A plurality of reactors are connected in parallel, the plurality of reactors connected in parallel are respectively connected with a condensation section and an isomerization section, when quality of the catalysts in the condensation reaction section does not meet requirements, the catalysts in the reactors are withdrawn and replaced with new modified catalysts, and the new modified catalysts are switched to the isomerization section to continue to be used. However, the method cannot solve the problem of waste caused by the fact that all the catalysts need to be replaced when quality of products is unstable during trial operation of each stage of reaction system, and it is necessary to remove the catalysts in full load in all the reactors connected in parallel once the quality of the products is not qualified during trial operation, resulting in huge economic loss. The present disclosure can solve the above problem, and has better advantages of avoiding economic losses especially for a large-scale preparation device.

SUMMARY

The present disclosure aims to provide a continuous and stable bisphenol A preparation process and device thereof. A resin catalyst is adopted, and a reaction system in which three reactors are connected in series is established. The established reaction system can provide higher reaction selectivity and conversion rate, and meanwhile is beneficial to improving production capacity. Due to process configuration of the reaction system and a filling solution for resin catalysts in the reactors, the present disclosure solves catalyst waste during startup and trial operation when products do not meet the quality requirements, and also the problems of decrease in production capacity and decrease in selectivity of bisphenol A caused by deactivation of the resin catalysts section by section can be avoided, thereby effectively reducing emissions of three wastes (wastewater, waste gases and solid wastes). A technical solution of the present disclosure is as follows:

a bisphenol A preparation process, includes two stages of reaction systems and an interstage dehydration system, each stage of reaction system includes a cooler and four reactors, each with four sections, the reactors are filled with bisphenol A synthetic resin catalysts before startup operation of each stage of reaction system, and filling proportions of the catalysts are as follows: ⅓ of the catalyst amount for the first-section reactor, ⅔ for the second-section reactor, the full amount for the third-section reactor and the full amount for the fourth-section reactor. The first-section reactor, the second-section reaction and the third-section reactor operate in series connection through valves, reaction raw materials enter an inlet of the first-section reactor, and products are extracted from an outlet of the third-section reactor.

According to the bisphenol A preparation process, any three reactors are capable of operating in series connection, and the remaining reactor can independently stop operating without affecting an overall process flow; the filling proportions of the catalysts in the reactors before startup operation of each stage of reaction system are as follows: ⅓ of the catalyst amount for the first-section reactor, ⅔ for the second-section reactor, the full amount for the third-section reactor and the full amount for the fourth-section reactor respectively; after startup operation of each stage of reaction system, the reactor with the deactivated catalyst is controlled to be cut out through a valve every ⅓ of the service life of the catalyst amount, and the remaining three reactors are controlled to operate in series to achieve continuous preparation.

According to the bisphenol A preparation process, a switching scheme of the reactors during operation of two stages of reaction systems is as follows:

1) Acetone, excess phenol and first-stage reaction liquid circulating streams are cooled to a reaction temperature and then fed into a first-stage reaction system for a reaction for generating bisphenol A to obtain mixed liquid of bisphenol A, unreacted phenol and byproducts, and part of the mixed liquid circulates back to the first-stage reaction system in proportion, such that a temperature of materials from an outlet of the first-stage reaction system is reduced below 76° C.; reaction liquid sent by the first-stage reaction system and reaction circulating liquid of a second-stage reaction system enter the interstage dehydration system to be subjected to vacuum flash evaporation and dehydration after being preheated, and then are fed into the second-stage reaction system; and the materials are cooled with fresh acetone supplemented at a feed inlet of the second-stage reaction system, the materials and the fresh acetone react in the second-stage reaction system to obtain bisphenol A, the bisphenol A reaction liquid is divided into two streams, one stream circulates back to the interstage dehydration system, the other stream is extracted and fed onto an adsorption column, and a temperature of the materials from outlets of second-stage reactors is reduced below 80° C. by adjusting a flow ratio of the stream circulating back to the interstage dehydration system to the stream extracted and fed onto an adsorption column.

2) When the catalyst in the first-section reactor is deactivated, the service life of the catalyst in the second-section reactor with the filling proportion of the ⅔ times of the catalyst reduced to ⅓ times, and the service life of the catalyst in the third-section reactor with the filling proportion of 1 time the catalyst has ⅔ remaining; at this moment, the first-section reactor with the deactivated catalyst is cut out through a valve, the fourth-section reactor is cut in to be connected with the second-section reactor and the third-section reactor in series, the reaction raw materials are input from the second-section reactor, the reaction products are extracted from the fourth-section reactor, the deactivated catalyst in the cut-out first-section reactor is discharged, and the first-section reactor is filled with a new catalyst with the filling proportion of 1 for later use;

3) when the catalyst in the second-section catalyst is deactivated, the second-section reactor with the deactivated catalyst is cut out through a valve, the first-section reactor is cut in to be connected with the third-section reactor and the fourth-section reactor in series, the deactivated catalyst in the cut-out second-section reactor is discharged, and the second-section reactor is filled with a new catalyst for later use; the raw materials are input from an inlet of the third-section reactor and extracted from an outlet of the first-section reactor;

4) when the catalyst in the third-section catalyst is deactivated, the third-section reactor with the deactivated catalyst is cut out through a valve, the second-section reactor is cut in through a value to be connected with the third-section reactor and the fourth-section reactor in series, the deactivated catalyst in the cut-out third-section reactor is discharged, and the third-section reactor is filled with a new catalyst for later use; the raw materials are input from an inlet of the fourth-section reactor and extracted from an outlet of the second-section reactor;

5) when the catalyst in the fourth-section catalyst is deactivated, the fourth-section reactor with the deactivated catalyst is cut out through a valve, the third-section reactor is cut in through a value to be connected with the first-section reactor and the second-section reactor in series, the deactivated catalyst in the cut-out fourth-section reactor is discharged, and the fourth-section reactor is filled with a new catalyst for later use; and the raw materials are input from the inlet of the first-section reactor; and extracted from the outlet of the third-section reactor, and two stages of reaction systems return to an initial state in terms of an operating mode.

The catalyst is the bisphenol A synthetic resin catalyst including sulphydryl modified strong-acid cation exchange resin.

In a device for realizing the bisphenol A preparation process according to the present disclosure, each reactor is provided with a raw material inlet and a product outlet, an inlet of each reactor in a first-stage reaction system is connected with an outlet of a first-stage cooler, an outlet of each reactor is respectively connected with an inlet of a first-stage circulating heat extraction pump and an inlet of an interstage preheater, an outlet of a first-stage first-section reactor is connected with an inlet of a first-stage second-section reactor, an outlet of the first-stage second-section reactor is connected with an inlet of a first-stage third-section reactor, an outlet of the first-stage third-section reactor is connected with an inlet of a first-stage fourth-section reactor, an outlet of the first-stage fourth-section reactor is connected with an inlet of the first-stage first-section reactor, an outlet of the first-stage circulating heat extraction pump is connected with an inlet of the first-stage cooler, an outlet of the interstage preheater is connected with an inlet of a dehydration flash tank, a gaseous phase outlet of the dehydration flash tank is connected with an inlet of a first-stage condenser, an outlet of the first-stage condenser is respectively connected with a recovery system and an inlet of a second-stage condenser, an outlet of the second-stage condenser is respectively connected with the recovery system and a vacuum unit, a liquid phase outlet of the dehydration flash tank is connected with an inlet of a flash liquid pump, an outlet of the flash liquid pump is connected with an inlet of a second-stage cooler, an acetone raw material pipeline is respectively connected with the inlet of the first-stage cooler and the inlet of the second-stage cooler, and a phenol raw material pipeline is connected with the inlet of the first-stage cooler; an inlet of each reactor in a second-stage reaction system is connected with an outlet of the second-stage cooler, an outlet of each reactor is respectively connected with the inlet of the interstage preheater and an inlet of an adsorption column, an outlet of a second-stage first-section reactor is connected with an inlet of a second-stage second-section reactor, and an outlet of the second-stage second-section reactor is connected with an inlet of a second-stage third-section reactor; an outlet of the second-stage third-section reactor is connected with an inlet of a second-stage fourth-section reactor, and an outlet of the second-stage fourth-section reactor is connected with an inlet of the second-stage first-section reactor; pipelines in each stage of reaction system are controlled to be connected or disconnected through valves, such that any three reactors can be connected in series; and an outlet of the adsorption column is connected with an inlet of a bisphenol A concentration system.

A bisphenol A synthesis process according to the present disclosure is as follows:

An outlet temperature on a cooling side of the first-stage cooler ranges from 65° C. to 70° C.; a unit bed pressure drop of the first-stage reactors connected in series ranges from 15 kPa/m to 30 kPa/m; outlet temperatures of the first-stage reactors connected in series are less than 76° C., and an outlet temperature of the first-stage circulating heat extraction pump ranges from 72° C. to 76° C.;

an outlet temperature on a cooling side of the second-stage cooler ranges from 65° C. to 70° C.; a unit bed pressure drop of the second-stage reactors connected in series ranges from 7 kPa/m to 28 kPa/m; outlet temperatures of the second-stage reactors connected in series range from 72° C. to 80° C.;

an outlet temperature on a heating side of the interstage preheater ranges from 85° C. to 90° C.; and a pressure of the dehydration flash tank ranges from 3 kPaA to 7 kPaA.

A flow ratio of material flow from the outlets of the second-stage reactors entering the interstage dehydration system to material flow fed onto the adsorption column ranges from 0.8:1 to 1:1.

The present disclosure has the following advantages and beneficial effects:

The present disclosure relates to a novel bisphenol A preparation process and device thereof, having the advantages that influences of external diffusion on the reaction are lowered, higher reaction selectivity and conversion rate are provided, and the production capacity of the process is improved; part of reaction heat can be removed through material circulation, such that the synthetic reaction for the bisphenol A stably operates at an appropriate temperature; water generated by the reaction is removed by the interstage dehydration system, and the reaction is promoted to be carried out forward, which is conducive to improving the selectivity and yield of the bisphenol A; and by the adoption of the proportional filling solution for the catalysts before startup operation of each stage of reaction system, the problem of catalyst waste caused when product quality is not up to standard during the startup and trial operation of each stage of reaction system is solved, the process and device thereof can ensure that the reaction continuously and stably proceeds under high catalytic activity, and decrease in the production capacity of the device and decrease in the selectivity of the bisphenol A are avoided, thereby effectively reducing the emissions of the three wastes. Meanwhile, by means of the anion resin adsorption column, the reaction liquid can be effectively prevented from containing acids, such that acidity of each stage of reaction system is well controlled.

BRIEF DESCRIPTION OF THE DRAWINGS

FIG. 1 is a flowchart of a bisphenol A synthesis process according to the present disclosure.

Wherein, 101: first-stage first-section reactor, 102: first-stage second-section reactor, 103: first-stage third-section reactor; 104: first-stage fourth-section reactor, 105: second-stage first-section reactor, 106: second-stage second-section reactor, 107: second-stage third-section reactor, 108: second-stage fourth-section reactor, 109: first-stage cooler, 110- interstage preheater, 111: second-stage cooler, 112: first-stage condenser, 113: second-stage condenser, 114: dehydration flash tank, 115: first-stage circulating heat extraction pump, 116: flash liquid pump, and 117: adsorption column.

DETAILED DESCRIPTION OF THE PRESENT DISCLOSURE

The present disclosure is further described in detail below with reference to FIG. 1 and specific embodiments. The following embodiments are merely descriptive and not restrictive, and do not limit the scope of protection of the present disclosure.

Illustration is made by taking a bisphenol A synthesis catalyst most commonly used at present, namely "sulphydryl modified strong-acid cation exchange resin" with a 12-month service life as an example.

The present disclosure provides a bisphenol A synthesis process, including the following technical solution:
(1) including a step of determining filling proportions of catalysts in reactors before each stage of reaction system is started up;
(2) including a step of cooling acetone and excess phenol and then feeding the same into a first-stage reaction system for a reaction to generate bisphenol A;
(3) including a step of feeding part of products from the first-stage reaction system back to the first-stage reaction system and feeding extracted streams into an interstage dehydration system for flash evaporation and dehydration;
(4) including a step of supplementing acetone and reacting in a second-stage reaction system to generate bisphenol A; and
(5) including a step of operating reactors in the two stages of reaction systems in series and switching the reactors after a fixed operational period.

The present disclosure provides a device for realizing the bisphenol A preparation process, including a first-stage first-section reactor 101, a first-stage second-section reactor 102, a first-stage third-section reactor 103, a first-stage fourth-section reactor 104, a second-stage first-section reactor 105, a second-stage second-section reactor 106, a second-stage third-section reactor 107, a second-stage fourth-section reactor 108, a first-stage cooler 109, an interstage preheater 110, a second-stage cooler 111, a first-stage condenser 112, a second-stage condenser 113, a dehydration flash tank 114, a first-stage circulating heat extraction pump 115, a flash liquid pump 116, and an adsorption column 117.

A connection mode of the two stages of reaction systems is as follows: each reactor is provided with a raw material inlet and a product outlet, an inlet of each reactor in the first-stage reaction system is connected with an outlet of the first-stage cooler 109, an outlet of each reactor is respectively connected with an inlet of the first-stage circulating heat extraction pump 115 and an inlet of the interstage preheater 110, an outlet of the first-stage first-section reactor 101 is connected with an inlet of the first-stage second-section reactor 102, an outlet of the first-stage second-section reactor 102 is connected with an inlet of the first-stage third-section reactor 103, an outlet of the first-stage third-section reactor 103 is connected with an inlet of the first-stage fourth-section reactor 104, an outlet of the first-stage fourth-section reactor 104 is connected with an inlet of the first-stage first-section reactor 101, an outlet of the first-stage circulating heat extraction pump 115 is connected with an inlet of the first-stage cooler 109, an outlet of the interstage preheater 110 is connected with an inlet of the dehydration flash tank 114, a gaseous phase outlet of the dehydration flash tank 114 is connected with an inlet of the first-stage condenser 112, an outlet of the first-stage condenser 112 is respectively connected with a recovery system and an inlet of the second-stage condenser 113, an outlet of the second-stage condenser 113 is respectively connected with the recovery system and a vacuum unit, a liquid phase outlet of the dehydration flash tank 114 is connected with an inlet of the flash liquid pump 116, an outlet of the flash liquid pump 116 is connected with an inlet of the second-stage cooler 111, an acetone raw material pipeline is respectively connected with the inlet of the first-stage cooler 109 and the inlet of the second-stage cooler 111, and a phenol raw material pipeline is connected with the inlet of the first-stage cooler 109; an inlet of each reactor in the second-stage reaction system is connected with an outlet of the second-stage cooler 111, an outlet of each reactor is respectively connected with the inlet of the interstage preheater 110 and an inlet of the adsorption column 117, an outlet of the second-stage first-section reactor 105 is connected with an inlet of the second-stage second-section reactor 106, and an outlet of the second-stage second-section reactor 106 is connected with an inlet of the second-stage third-section reactor 107; an outlet of the second-stage third-section reactor 107 is connected with an inlet of the second-stage fourth-section reactor 108, and an outlet of the second-stage fourth-section reactor 108 is connected with an inlet of the second-stage first-section reactor 105; pipelines in each stage of reaction system are controlled to be connected or disconnected through valves, such that any three reactors can be connected in series; and an outlet of the adsorption column 117 is connected with an inlet of a bisphenol A concentration system through a pipeline.

In the above technical solution, a specific implementation of step (1) is as follows: the reactors in the two stages of reaction systems are filled with the sulphydryl modified strong-acid cation exchange resin catalysts for the synthesis of Bisphenol A in advance before startup operation of each stage of reaction system, and filling proportions of the first-stage reaction system are as follows: ⅓ of the catalysts for the first-stage first-section reactor, ⅔ for the first-stage second-section reactor, the full amount for the first-stage third-section reactor, and the full amount for the first-stage fourth-section reactor; and filling proportions of the second-stage reaction system are as follows: ⅓ of the catalysts for the second-stage first-section reactor, ⅔ for the second-stage second-section reactor, the full amount for the second-stage third-section reactor, and the full amount for the second-stage fourth-section reactor.

In the above technical solution, a specific implementation of step (2) is as follows: the acetone and the excess phenol are introduced into the cooler to be cooled to 70° C., and then fed into the first-stage reaction system for the condensation reaction to generate bisphenol A mixed liquid.

In the above technical solution, a specific implementation of step (3) is as follows: part of the mixed liquid in step (2) is fed into the first-stage circulating heat extraction pump to return to the first-stage reaction system to continue to participate in the reaction, a flow ratio is adjusted to make an outlet temperature of the first-stage circulating heat extraction pump less than 76° C., and the remaining mixed liquid is preheated by the interstage preheater to 85° C., and then fed into the vacuum dehydration flash tank for dehydration.

In the above technical solution, a specific implementation of step (4) is as follows: material flow from the liquid phase outlet of the dehydration flash tank is fed into the inlet of the flash liquid pump, and material flow from the outlet of the flash liquid pump is mixed with acetone raw materials and then cooled by the second-stage cooler to 70° C., and then enter the second-stage reactors for the reaction.

In the above technical solution, a specific implementation of step (5) is as follows:

After startup operation of the two stages of reaction systems for 4 months, in each of the two stages of reaction systems, the catalyst in the first-section reactor with the filling proportion of the catalyst of ⅓ is deactivated before startup, the service life of the catalyst in the second-section reactor with the filling proportion of the catalyst of ⅔ has 4 months remaining, the service life of the catalyst in the third-section reactor with the filling proportion of the catalyst of 1 has 8 months remaining, and the service life of the catalyst in the fourth-section reactor with the filling proportion of the catalyst of 1 has 12 months remaining. At this moment, the first-section reactor with the deactivated catalyst cut out through the valve, the fourth-section reactor is cut in to be connected with the second-section reactor and the third-section reactor in series, the reaction raw materials are input from the second-section reactor where the catalyst has a remaining service life of 4 months, the reaction products are extracted from the fourth-section reactor where the catalyst has a remaining service life of 12 months, the deactivated catalyst in the cut-out first-section reactor is discharged, and the first-section reactor is filled with a new sulphydryl modified strong-acid cation exchange resin catalyst for later use.

After startup operation of the two stages of reaction systems for 8 months, the catalyst in the second-section catalyst is deactivated, the second-section reactor with the deactivated catalyst is cut out through the valve, the first-section reactor is cut in to be connected with the third-section reactor and the fourth-section reactor in series, the deactivated catalyst in the cut-out second-section reactor is discharged, and the second-section reactor is filled with a new sulphydryl modified strong-acid cation exchange resin catalyst for later use, and the raw materials are input from the inlet of the third-section reactor and extracted from the outlet of the first-section reactor.

After startup operation of the two stages of reaction systems for 12 months, the catalyst in the third-section catalyst is deactivated, the third-section reactor with the deactivated catalyst is cut out through the valve, the second-section reactor is cut in to be connected with the first-section reactor and the fourth-section reactor in series, the deactivated catalyst in the cut-out third-section reactor is discharged, the third-section reactor is filled with a new sulphydryl modified strong-acid cation exchange resin catalyst for later use, and the raw materials are input from the inlet of the fourth-section reactor and extracted from the outlet of the second-section reactor.

After startup operation of the two stages of reaction systems for 16 months, the catalyst in the fourth-section catalyst is deactivated, the fourth-section reactor with the deactivated catalyst is cut out through the valve, the third-section reactor is cut in to be connected with the first-section reactor and the second-section reactor in series, the deactivated catalyst in the cut-out fourth-section reactor is discharged, the fourth-section reactor is filled with a new sulphydryl modified strong-acid cation exchange resin catalyst for later use, the raw materials are input from the inlet of the first-section reactor and extracted from the outlet of the third-section reactor, and the two stages of reaction systems return to a state before startup in terms of an operating mode.

Thus, the reactor with the deactivated catalyst is cut out every 4 months, the catalyst in the reactor is discharged, the reactor is filled with the new catalyst for later use, and the remaining three reactors are maintained operating in series by controlling the valves, thereby achieving continuous and stable process preparation.

FIG. 1 is a flowchart of a bisphenol A synthesis process according to the present disclosure.

An outlet temperature on a cooling side of the first-stage cooler ranges from 65° C. to 70° C.; a unit bed pressure drop of the first-stage reactors connected in series ranges from 15 kPa/m to 30 kPa/m; outlet temperatures of the first-stage reactors connected in series are less than 76° C., and an outlet temperature of the first-stage circulating heat extraction pump ranges from 72° C. to 76° C.; an outlet temperature on a cooling side of the second-stage cooler ranges from 65° C. to 70° C.; a unit bed pressure drop of the second-stage reactors connected in series ranges from 7 kPa/m to 28 kPa/m; outlet temperatures of the second-stage reactors connected in series range from 72° C. to 80° C.; an outlet temperature on a heating side of the interstage preheater ranges from 85° C. to 90° C.; and a pressure of the dehydration flash tank ranges from 3 kPaA to 7 kPaA. A flow ratio of the material flow from the outlets of the second-stage reactors entering the interstage dehydration system to the material flow fed onto the adsorption column ranges from 0.8:1 to 1:1.

The specific implementation process of the method of the present application is described below with the specific embodiments.

EMBODIMENT 1

When the two stages of reaction systems are started up, raw materials of phenol and acetone and circulating products from the first-stage reaction system are mixed and cooled by the first-stage cooler 109 to 65° C., and then the mixture sequentially enters the first-stage first-section reactor 101, the first-stage second-section reactor 102 and the first-stage third-section reactor 103 connected in series for the condensation reaction, wherein the filling portions of the catalysts are as follows: ⅓ of the catalysts for the first-stage first-section reactor 101, ⅔ for the first-stage second-section reactor 102, the full amount for the first-stage third-section reactor 103 and the full amount for the first-stage fourth-section reactor 104. The first-stage fourth-section reactor 104 is temporarily disconnected from the first-stage reaction system through the valve, the unit bed pressure drop of the three reactors connected in series is 15 kPa/m, the temperature of materials from the outlet of the first-stage third-section reactor is 76° C., products from the outlet of the first-stage third-section reactor 103 respectively enter the first-stage circulating heat extraction pump 115 and the interstage preheater 110 in a ratio of 2:1, the outlet temperature of the first-stage circulating heat extraction pump is 73° C., the reaction liquid heated by the interstage preheater 110 to 85° C. enters the dehydration flash tank 114 for flash evaporation and dehydration at a pressure of 3 kPaA, water and light-component byproducts from the gaseous phase outlet of the dehydration flash tank 114 enter a recovery system section after passing through the first-stage condenser 112 and the second-stage condenser 113, products from the liquid phase outlet of the dehydration flash tank 114 are mixed with supplemented fresh acetone after passing through the flash liquid pump, and then fed into the second-stage cooler 111 to be cooled to 65° C., the reaction liquid of the products and the fresh acetone sequentially enters the second-stage first-section reactor 105, the second-stage second-section reactor 106 and the second-stage third-section reactor 107 connected in series for the condensation reaction after being cooled in the second-stage cooler, the filling proportions of the catalysts are as follows: ⅓ of the catalysts for the second-stage first-section reactor 105, ⅔ for the second-stage second-section reactor 106, the full amount for the second-stage third-section reactor 107 and the full amount for the second-stage fourth-section reactor 108, a pipeline connected with the second-stage fourth-section reactor 108 is disconnected from the second-stage fourth-section reactor through the valve, the second-stage fourth-section reactor 108 is independently placed for later use accordingly, the unit bed pressure drop of the three reactors connected in series is 7 kPa/m, and the temperature of materials from the outlet of the second-stage third-section reactor is 80° C. Products from the outlet of the second-stage third-section reactor 107 respectively enter the inlet of the interstage preheater 110 and the inlet of the adsorption column 117 in a ratio of 0.8:1.

After the two stages of reaction systems operate for 4 months, the catalysts in the first-stage first-section reactor 101 and the second-stage first-section reactor 105 with the filling proportions of the catalysts of ⅓ are deactivated, the service life of the catalysts in the first-stage second-section reactor 102 and the second-stage second-section reactor 106 with the filling proportions of the catalysts of ⅔ has 4 months remaining, the service life of the catalysts in the first-stage third-section reactor 103 and the service life of the second-stage third-section reactor 107 with the filling proportions of the catalysts of 1 have 8 months remaining, and the service life of the catalysts in the first-stage fourth-section reactor 104 and the service life of the second-stage fourth-section reactor 108 have 12 months remaining. At this moment, the first-stage first-section reactor 101 and the second-stage first-section reactor 105 with the deactivated catalysts are cut out through the valves, the first-stage fourth-section reactor 104 is started up to be connected with the first-stage second-section reactor 102 and the first-stage third-section reactor 103 in series, the raw material inlet valve of the first-stage second-section reactor 102 and the product outlet valve of the first-stage fourth-section reactor 104 are opened to control raw material input and product output of the first-stage reaction system, the second-stage fourth-section reactor 108 is started up to be connected with the second-stage second-section reactor 106 and the second-stage third-section reactor 107 in series in the second-stage reaction system, the raw material inlet valve of the second-stage second-section reactor 106 and the product outlet valve of the second-stage fourth-section reactor 108 are opened to control raw material input and product output of the second-stage reaction system, and the deactivated catalysts in the cut-out first-stage first-section reactor 101 and second-stage first-section reactor 105 are evaluated and discharged, and the first-stage first-section reactor and the second-stage first-section reactor are filled with a new catalyst (proportion of 1) for later use.

After the two stages of reaction systems operate for 8 months, the first-stage second-section reactor 102 and the second-stage second-section reactor 106 with the deactivated catalysts are cut out through the valves, the first-stage first-section reactor 101 is connected with the first-stage third-section reactor 103 and the first-stage fourth-section reactor 104 in series, the raw material inlet valve of the first-stage third-section reactor 103 and the product outlet valve of the first-stage first-section reactor 101 are opened to control raw material input and product output of the first-stage reaction system, the second-stage first-section reactor 105 is connected with the second-stage third-section reactor 107 and the second-stage fourth-section reactor 108 in series, the raw material inlet valve of the second-stage third-section reactor 107 and the product outlet valve of the second-stage first-section reactor 105 are opened to control raw material input and product output of the second-stage reaction system, the deactivated catalysts in the first-stage second-section reactor 102 and the second-stage second-section reactor 106 are discharged, and then the first-stage second-section reactor and the second-stage second-section reactor are filled with a new catalyst (proportion of 1) for later use.

After the two stages of reaction systems operate for 12 months, the first-stage third-section reactor 103 and the second-stage third-section reactor 107 with the deactivated catalysts are cut out through the valves, the first-stage second-section reactor 102 is connected with the first-stage fourth-section reactor 104 and the first-stage first-section reactor 101 in series, the raw material inlet valve of the first-stage fourth-section reactor 104 and the product outlet valve of the first-stage second-section reactor 102 are opened to control raw material input and product output of the first-stage reaction system, the second-stage second-section reactor 106 is connected with the second-stage fourth-section reactor 108 and the second-stage first-section reactor 105 in series, the raw material inlet valve of the second-stage fourth-section reactor 108 and the product outlet valve of the second-stage second-section reactor 106 are opened to control raw material input and product output of the second-stage reaction system, the deactivated catalysts in the first-stage third-section reactor 103 and the second-stage third-section reactor 107 are discharged, and then the first-stage third-section reactor and the second-stage third-section reactor are filled with a new catalyst (proportion of 1) for later use.

After the two stages of reaction systems operate for 16 months, the first-stage fourth-section reactor 104 and the second-stage fourth-section reactor 108 with the deactivated catalysts are cut out through the valves, the first-stage third-section reactor 103 is connected with the first-stage first-section reactor 101 and the first-stage second-section reactor 102 in series, the raw material inlet valve of the first-stage first-section reactor 101 and the product outlet valve of the first-stage third-section reactor 103 are opened to control raw material input and product output of the first-stage reaction system, the second-stage third-section reactor 107 is connected with the second-stage first-section reactor 105 and the second-stage second-section reactor 106 in series, the raw material inlet valve of the second-stage first-section reactor 105 and the product outlet valve of the second-stage third-section reactor 107 are opened to control raw material input and product output of the second-stage reaction system, the deactivated catalysts in the first-stage fourth-section reactor 104 and the second-stage fourth-section reactor 108 are discharged, and then the first-stage fourth-section reactor and the second-stage fourth-section reactor are filled with a new catalyst (proportion of 1) for later use. At this moment, the two stages of reaction systems return to a first startup operation state again. The operation is repeated in this way, the reactor with the deactivated catalyst is cut out every 4 months, the catalyst in the reactor is discharged, the reactor is filled with the new catalyst for later use, and the remaining three reactors are maintained operating in series by controlling the valves, thereby achieving continuous and stable process preparation.

According to the process capable of annually outputting 460,000 tons of bisphenol A in this embodiment, the conversion rate of the first-stage reaction system is 99.5%, the selectivity is 96.8%, the conversion rate of the second-stage reaction system is 99.4%, and the selectivity is 97%.

EMBODIMENT 2

When the two stages of reaction systems are started up, raw materials of phenol and acetone and circulating products from the first-stage reaction system are mixed and cooled by the first-stage cooler 109 to 68° C., and then the mixture sequentially enters the first-stage first-section reactor 101, the first-stage second-section reactor 102 and the first-stage third-section reactor 103 connected in series for the condensation reaction, wherein the filling portions of the catalysts are as follows: ⅓ of the catalysts for the first-stage first-section reactor 101, ⅔ for the first-stage second-section reactor 102, the full amount for the first-stage third-section reactor 103 and the full amount for the first-stage fourth-section reactor 104. The first-stage fourth-section reactor 104 is temporarily disconnected from the first-stage reaction system through the valve, the unit bed pressure drop of the three reactors connected in series is 25 kPa/m, the temperature of materials from the outlet of the first-stage third-section reactor is 76° C., products from the outlet of the first-stage third-section reactor 103 respectively enter the first-stage circulating heat extraction pump 115 and the interstage preheater 110 in a ratio of 2.1:1, the outlet temperature of the first-stage circulating heat extraction pump is 73° C., the reaction liquid heated by the interstage preheater 110 to 87° C. enters the dehydration flash tank 114 for flash evaporation and dehydration at a pressure of 5 kPaA, water and light-component byproducts from the gaseous phase outlet of the dehydration flash tank 114 enter a recovery system section after passing through the first-stage condenser 112 and the second-stage condenser 113, products from the liquid phase outlet of the dehydration flash tank 114 are mixed with supplemented fresh acetone after passing through the flash liquid pump, and then fed into the second-stage cooler 111 to be cooled to 68° C., the reaction liquid of the products and the fresh acetone sequentially enters the second-stage first-section reactor 105, the second-stage second-section reactor 106 and the second-stage third-section reactor 107 connected in series for the condensation reaction after being cooled in the second-stage cooler, the filling proportions of the catalysts are as follows: ⅓ of the catalysts for the second-stage first-section reactor 105, ⅔ for the second-stage second-section reactor 106, the full amount for the second-stage third-section reactor 107 and the full amount for the second-stage fourth-section reactor 108, a pipeline connected with the second-stage fourth-section reactor 108 is disconnected from the second-stage fourth-section reactor through the valve, the second-stage fourth-section reactor 108 is independently placed for later use, the unit bed pressure drop of the three reactors connected in series is 23 kPa/m, and the temperature of materials from the outlet of the second-stage third-section reactor is 76° C. Products from the outlet of the second-stage third-section reactor 107 respectively enter the inlet of the interstage preheater 110 and the inlet of the adsorption column 117 in a ratio of 0.9:1.

After the two stages of reaction systems operate for 5 months, the catalysts in the first-stage first-section reactor 101 and the second-stage first-section reactor 105 with the filling proportions of the catalysts of ⅓ are deactivated, the service life of the catalysts in the first-stage second-section reactor 102 and the second-stage second-section reactor 106 with the filling proportions of the catalysts of ⅔ has 5 months remaining, the service life of the catalysts in the first-stage third-section reactor 103 and the second-stage third-section reactor 107 with the filling proportions of the catalysts of 1 has 10 months remaining, and the service life of the catalysts in the first-stage fourth-section reactor 104 and the second-stage fourth-section reactor 108 has 15 months remaining. At this moment, the first-stage first-section reactor 101 and the second-stage first-section reactor 105 with the deactivated catalysts are cut out through the valves, the first-stage fourth-section reactor 104 is started up to be connected with the first-stage second-section reactor 102 and the first-stage third-section reactor 103 in series, the raw material inlet valve of the first-stage second-section reactor 102 and the product outlet valve of the first-stage fourth-section reactor 104 are opened to control raw material input and product output of the first-stage reaction system, the second-stage fourth-section reactor 108 is started up to be connected with the second-stage second-section reactor 106 and the second-stage third-section reactor 107 in series in the second-stage reaction system, the raw material inlet valve of the second-stage second-section reactor 106 and the product outlet valve of the second-stage fourth-section reactor 108 are opened to control raw material input and product output of the second-stage reaction system, and the deactivated catalysts in the cut-out first-stage first-section reactor 101 and second-stage first-section reactor 105 are evaluated and discharged, and then the first-stage first-section reactor and the second-stage first-section reactor are filled with a new catalyst (proportion of 1) for later use.

After the two stages of reaction systems operate for 10 months, the first-stage second-section reactor 102 and the second-stage second-section reactor 106 with the deactivated catalysts are cut out through the valves, the first-stage first-section reactor 101 is connected with the first-stage third-section reactor 103 and the first-stage fourth-section reactor 104 in series, the raw material inlet valve of the first-stage third-section reactor 103 and the product outlet valve of the first-stage first-section reactor 101 are opened to control raw material input and product output of the first-stage reaction system, the second-stage first-section reactor 105 is connected with the second-stage second-section reactor 106 and the second-stage fourth-section reactor 108 in series, the raw material inlet valve of the second-stage third-section reactor 107 and the product outlet valve of the second-stage first-section reactor 105 are opened to control raw material input and product output of the second-stage reaction system, the deactivated catalysts in the first-stage second-section reactor 102 and the second-stage second-section reactor 106 are evaluated and discharged, and then the first-stage second-section reactor and the second-stage second-section reactor are filled with a new catalyst (proportion of 1) for later use.

After the two stages of reaction systems operate for 15 months, the first-stage third-section reactor 103 and the second-stage third-section reactor 107 with the deactivated catalysts are cut out through the valves, the first-stage second-section reactor 102 is connected with the first-stage fourth-section reactor 104 and the first-stage first-section reactor 101 in series, the raw material inlet valve of the first-stage fourth-section reactor 104 and the product outlet valve of the first-stage second-section reactor 102 are opened to control raw material input and product output of the first-stage reaction system, the second-stage second-section reactor 106 is connected with the second-stage fourth-section reactor 108 and the second-stage first-section reactor 105 in series, the raw material inlet valve of the second-stage fourth-section reactor 108 and the product outlet valve of the second-stage second-section reactor 106 are opened to control raw material input and product output of the second-stage reaction system, the deactivated catalysts in the first-stage third-section reactor 103 and the second-stage third-section reactor 107 are discharged, and then the first-stage third-section reactor and the second-stage third-section reactor are filled with a new catalyst (proportion of 1) for later use.

After the two stages of reaction systems operate for 20 months, the first-stage fourth-section reactor 104 and the second-stage fourth-section reactor 108 with the deactivated catalysts are cut out through the valves, the first-stage third-section reactor 103 is connected with the first-stage first-section reactor 101 and the first-stage second-section reactor 102 in series, the raw material inlet valve of the first-stage first-section reactor 101 and the product outlet valve of the first-stage third-section reactor 103 are opened to control raw material input and product output of the first-stage reaction system, the second-stage third-section reactor 107 is connected with the second-stage first-section reactor 105 and the second-stage second-section reactor 106 in series, the raw material inlet valve of the second-stage first-section reactor 105 and the product outlet valve of the second-stage third-section reactor 107 are opened to control raw material input and product output of the second-stage reaction system, the deactivated catalysts in the first-stage fourth-section reactor 104 and the second-stage fourth-section reactor 108 are discharged, and then the first-stage fourth-section reactor and the second-stage fourth-section reactor are filled with a new catalyst (proportion of 1) for later use. At this moment, the two stages of reaction systems return to a first startup operation state again. The operation is repeated in this way, the reactor with the deactivated catalyst is cut out every 5 months, the catalyst in the reactor is discharged, the reactor is filled with the new catalyst for later use, and the remaining three reactors in series maintain operation by controlling the valves, thereby achieving continuous and stable process preparation.

According to the process capable of annually outputting 470,000 tons of bisphenol A in this embodiment, the conversion rate of the first-stage reaction system is 99.6%, the selectivity is 97%, the conversion rate of the second-stage reaction system is 99.5%, and the selectivity is 97.4%.

EMBODIMENT 3

When the two stages of reaction systems are started up, raw materials of phenol and acetone and circulating products from the first-stage reaction system are mixed and cooled by the first-stage cooler 109 to 70° C., and then the mixture sequentially enters the first-stage first-section reactor 101, the first-stage second-section reactor 102 and the first-stage third-section reactor 103 connected in series for the condensation reaction, wherein the filling portions of the catalysts are as follows: ⅓ of the catalysts for the first-stage first-section reactor 101, ⅔ for the first-stage second-section reactor 102, the full amount for the first-stage third-section reactor 103 and the full amount for the first-stage fourth-section reactor 104. The first-stage fourth-section reactor 104 is temporarily disconnected from the reaction system through the valve, the unit bed pressure drop of the three reactors connected in series is 30 kPa/m, the temperature of materials from the outlet of the first-stage third-section reactor is 76° C., products from the outlet of the first-stage third-section reactor 103 respectively enter the first-stage circulating heat extraction pump 115 and the interstage preheater 110 in a ratio of 2.2:1, the outlet temperature of the first-stage circulating heat extraction pump is 75° C., the reaction liquid heated by the interstage preheater 110 to 90° C. enters the dehydration flash tank 114 for flash evaporation and dehydration at a pressure of 7 kPaA, water and light-component byproducts from the gaseous phase outlet of the dehydration flash tank 114 enter a recovery system section after passing through the first-stage condenser 112 and the second-stage condenser 113, products from the liquid phase outlet of the dehydration flash tank 114 are mixed with supplemented fresh acetone after passing through the flash liquid pump, and then fed into the second-stage cooler 111 to be cooled to 70° C., the reaction liquid of the products and the fresh acetone sequentially enters the second-stage first-section reactor 105, the second-stage second-section reactor 106 and the second-stage third-section reactor 107 connected in series for the condensation reaction after being cooled in the second-stage cooler, the filling proportions of the catalysts are as follows: ⅓ for the second-stage first-section reactor 105,⅔ for the second-stage second-section reactor 106, the full amount for the second-stage third-section reactor 107 and the full amount for the second-stage fourth-section reactor 108, a pipeline connected with the second-stage fourth-section reactor 108 is disconnected from the second-stage fourth-section reactor through the valve, the second-stage fourth-section reactor 108 is independently placed for later use, the unit bed pressure drop of the three reactors connected in series is 28 kPa/m, and the temperature of materials from the outlet of the second-stage third-section reactor is 80° C. Products from the outlet of the second-stage third-section reactor 107 respectively enter the inlet of the interstage preheater 110 and the inlet of the adsorption column 117 in a ratio of 1:1.

After the two stages of reaction systems operate for 6 months, the catalysts in the first-stage first-section reactor 101 and the second-stage first-section reactor 105 with the filling proportions of the catalysts of ⅓ are deactivated, the service life of the catalysts in the first-stage second-section reactor 102 and the second-stage second-section reactor 106 with the filling proportions of the catalysts of ⅔ has 6 months remaining, the service life of the catalysts in the first-stage third-section reactor 103 and the second-stage third-section reactor 107 with the filling proportions of the catalysts of 1 has 12 months remaining, and the service life of the catalysts in the first-stage fourth-section reactor 104 and the second-stage fourth-section reactor 108 has 18 months remaining. At this moment, the first-stage first-section reactor 101 and the second-stage first-section reactor 105 with the deactivated catalysts are cut out through the valves, the first-stage fourth-section reactor 104 is started up to be connected with the first-stage second-section reactor 102 and the first-stage third-section reactor 103 in series, the raw material inlet valve of the first-stage second-section reactor 102 and the product outlet valve of the first-stage fourth-section reactor 104 are opened to control raw material input and product output of the first-stage reaction system, the second-stage fourth-section reactor 108 is started up to be connected with the second-stage second-section reactor 106 and the second-stage third-section reactor 107 in series in the second-stage reaction system, the raw material inlet valve of the second-stage second-section reactor 106 and the product outlet valve of the second-stage fourth-section reactor 108 are opened to control raw material input and product output of the second-stage reaction system, and the deactivated catalysts in the cut-out first-stage first-section reactor 101 and second-stage first-section reactor 105 are evaluated and discharged, and then the first-stage first-section reactor and the second-stage first-section reactor are filled with a new catalyst (proportion of 1) for later use.

After the two stages of reaction systems operate for 12 months, the first-stage second-section reactor 102 and the second-stage second-section reactor 106 with the deactivated catalysts are cut out through the valves, the first-stage first-section reactor 101 is connected with the first-stage third-section reactor 103 and the first-stage fourth-section reactor 104 in series, the raw material inlet valve of the first-stage third-section reactor 103 and the product outlet valve of the first-stage first-section reactor 101 are opened to control raw material input and product output of the first-stage reaction system, the second-stage first-section reactor 105 is connected with the second-stage third-section reactor 107 and the second-stage fourth-section reactor 108 in series, the raw material inlet valve of the second-stage third-section reactor 107 and the product outlet valve of the second-stage first-section reactor 105 are opened to control raw material input and product output of the second-stage reaction system, the deactivated catalysts in the first-stage second-section reactor 102 and the second-stage second-section reactor 106 are discharged, and then the first-stage second-section reactor and the second-stage second-section reactor are filled with a new catalyst (proportion of 1) for later use.

After the two stages of reaction systems operate for 18 months, the first-stage third-section reactor 103 and the second-stage third-section reactor 107 with the deactivated catalysts are cut out through the valves, the first-stage second-section reactor 102 is connected with the first-stage fourth-section reactor 104 and the first-stage first-section reactor 101 in series, the raw material inlet valve of the first-stage fourth-section reactor 104 and the product outlet valve of the first-stage second-section reactor 102 are opened to control raw material input and product output of the first-stage reaction system, the second-stage second-section reactor 106 is connected with the second-stage fourth-section reactor 108 and the second-stage first-section reactor 105 in series, the raw material inlet valve of the second-stage fourth-section reactor 108 and the product outlet valve of the second-stage second-section reactor 106 are opened to control raw material input and product output of the second-stage reaction system, the deactivated catalysts in the first-stage third-section reactor 103 and the second-stage third-section reactor 107 are discharged, and then the first-stage third-section reactor and the second-stage third-section reactor are filled with a new catalyst (proportion of 1) for later use.

After the two stages of reaction systems operate for 24 months, the first-stage fourth-section reactor 104 and the second-stage fourth-section reactor 108 with the deactivated catalysts are cut out through the valves, the first-stage third-section reactor 103 is connected with the first-stage first-section reactor 101 and the first-stage second-section reactor 102 in series, the raw material inlet valve of the first-stage first-section reactor 101 and the product outlet valve of the first-stage third-section reactor 103 are opened to control raw material input and product output of the first-stage reaction system, the second-stage third-section reactor 107 is connected with the second-stage first-section reactor 105 and the second-stage second-section reactor 106 in series, the raw material inlet valve of the second-stage first-section reactor 105 and the product outlet valve of the second-stage third-section reactor 107 are opened to control raw material input and product output of the second-stage reaction system, the deactivated catalysts in the first-stage fourth-section reactor 104 and the second-stage fourth-section reactor 108 are discharged, and then the first-stage fourth-section reactor and the second-stage fourth-section reactor are filled with a new catalyst (proportion of 1) for later use. At this moment, the two stages of reaction systems return to a first startup operation state again. The operation is repeated in this way, the reactor with the deactivated catalyst is cut out every 6 months, the catalyst in the reactor is discharged, the reactor is filled with the new catalyst for later use, and the remaining three reactors in series maintain operating by controlling the valves, thereby achieving continuous and stable process preparation.

According to the process capable of annually outputting 480,000 tons of bisphenol A in this embodiment, the conversion rate of the first-stage reaction system is 99.8%, the selectivity is 97.5%, the conversion rate of the second-stage reaction system is 99.6%, and the selectivity is 98%.

The present disclosure has the beneficial technical effects that a higher air speed can be provided by operating the reactors in series, the reaction conversion rate and selectivity are improved, and the preparation scale of the bisphenol A is expanded; and due to the solution for filling the catalysts in proportion, the catalysts can be conveniently evaluated and analyzed during trial operation of the two stages of reaction systems, loss of the catalysts is reduced, and therefore economic benefits of the process are increased.

Equipment unspecified in the present disclosure is conventional equipment, and it can be achieved by adopting methods and equipment well known to those skilled in the art. Although the present disclosure has been described with reference to the specific implementation solutions and drawings, the present disclosure is not expected to be limited to the specific form here. On the contrary, the scope of the present disclosure is only limited by the appended claims. In addition, although independent features may be included in different claims, these features may be advantageously combined, and the inclusion in different claims does not mean that the combination of features is not feasible and/or advantageous. References to "first", "second," etc., do not exclude plurals.

What is claimed is:

1. A bisphenol A preparation process, comprising two stages of reaction systems and an interstage dehydration system, wherein each stage of reaction system comprises a cooler and reactors, each with four sections, the reactors are filled with bisphenol A synthetic resin catalysts before startup operation of each stage of reaction system, and filling proportions of the catalysts are as follows: ⅓ of the catalysts for the first-section reactor, ⅔ for the second-section reactor, the full amount for the third-section reactor and the full amount for the fourth-section reactor; the first-section reactor, the second-section reactor and the third-section reactor operate in series connection through valves, reaction raw materials enter an inlet of the first-section reactor, and products are extracted from an outlet of the third-section reactor; any three reactors are capable of operating in series connection, and the remaining reactor can independently stop operating without affecting an overall process flow; the filling proportions of the catalysts in the reactors before startup operation of each stage of reaction system are as follows: ⅓ of the catalysts for the first-section reactor, ⅔ for the second-section reactor, the full amount for the third-section reactor and the full amount for the fourth-section reactor respectively, after startup operation of each stage of reaction system, the reactor with the deactivated catalyst is cut out through the valve every ⅓ of the service life of the catalyst, and the remaining three reactors are controlled to operate in series to achieve continuous preparation;

a switching scheme of the reactors during operation of two stages of reaction systems is as follows:
1) Acetone, excess phenol and reaction circulating streams are cooled and then fed into a first-stage reaction system for a bisphenol A synthesis reaction, to obtain mixed liquid of bisphenol A, unreacted phenol and byproducts, and part of the mixed liquid returns to the first-stage reaction system to serve as circulating streams, such that a temperature of materials sent out by the first-stage reaction system is reduced below 76° C.; the sent-out materials and circulating reaction liquid from a second-stage reaction system enter the interstage dehydration system to be subjected to vacuum flash evaporation and dehydration after being preheated; the dehydrated materials are fed into the second-stage reaction system and cooled together with fresh acetone supplemented at a feeding inlet of the second-stage reaction system, the dehydrated materials and the fresh acetone react in the second-stage reaction system, to obtain bisphenol A reaction liquid, the reaction liquid is divided into two streams, one stream circulates back to the interstage dehydration system, the other stream is extracted and fed onto an adsorption column, and a temperature of the materials from outlets of second-stage reactors is reduced below 80° C. by adjusting a flow ratio of the stream circulating back to the interstage dehydration system to the stream extracted and fed onto an adsorption column;
2) When the catalyst in the first-section reactor is deactivated, the service life of the catalyst in the second-section reactor with the filling proportion of the catalyst of ⅔ is ⅓, and the service life of the catalyst in the third-section reactor with the filling proportion of the catalyst of 1 has ⅔ remaining; at this moment, the first-section reactor with the deactivated catalyst is cut off through the valve, the fourth-section reactor is cut in to be connected with the second-section reactor and the third-section reactor in series, the reaction raw materials are input from the second-section reactor with the catalyst, the reaction products are extracted from the fourth-section reactor, the deactivated catalyst in the cut-out first-section reactor is discharged, and the first-section reactor is filled with a new catalyst with the filling proportion of 1 for later use;
3) When the catalyst in the second-section catalyst is deactivated, the second-section reactor with the deactivated catalyst is cut out through the valve, the first-section reactor is cut in to be connected with the third-section reactor and the fourth-section reactor in series, the deactivated catalyst in the cut-out second-section reactor is discharged, and the second-section reactor is filled with a new catalyst for later use; the raw materials are input from an inlet of the third-section reactor and extracted from an outlet of the first-section reactor;
4) When the catalyst in the third-section catalyst is deactivated, the third-section reactor with the deactivated catalyst is cut out through the valve, the second-section reactor is cut in to be connected with the first-section reactor and the fourth-section reactor in series, the deactivated catalyst in the cut-out third-section reactor is discharged, and the third-section reactor is filled with a new catalyst for later use; the raw materials are input from an inlet of the fourth-section reactor and extracted from an outlet of the second-section reactor;

5) When the catalyst in the fourth-section catalyst is deactivated, the fourth-section reactor with the deactivated catalyst is cut out through the valve, the third-section reactor is cut in to be connected with the first-section reactor and the second-section reactor in series, the deactivated catalyst in the cut-out fourth-section reactor is discharged, and the fourth-section reactor is filled with a new catalyst for later use; and the raw materials are input from the inlet of the first-section reactor and extracted from the outlet of the third-section reactor, and the two stages of reaction systems returns to an initial state in terms of an operating mode.

2. The bisphenol A preparation process according to claim 1, wherein the catalyst is the bisphenol A synthetic resin catalyst comprising sulphydryl modified strong-acid cation exchange resin.

3. A device for implementing the bisphenol A preparation process according to claim 1, wherein each reactor is provided with a raw material inlet and a product outlet, an inlet of each reactor in a first-stage reaction system is connected with an outlet of a first-stage cooler (109), an outlet of each reactor is respectively connected with an inlet of a first-stage circulating heat extraction pump (115) and an inlet of an interstage preheater (110), an outlet of a first-stage first-section reactor (101) is connected with an inlet of a first-stage second-section reactor (102), an outlet of the first-stage second-section reactor (102) is connected with an inlet of a first-stage third-section reactor (103), an outlet of the first-stage third-section reactor (103) is connected with an inlet of a first-stage fourth-section reactor (104), an outlet of the first-stage fourth-section reactor (104) is connected with an inlet of the first-stage first-section reactor (101), an outlet of the first-stage circulating heat extraction pump (115) is connected with an inlet of the first-stage cooler (109), an outlet of the interstage preheater (110) is connected with an inlet of a dehydration flash tank (114), a gaseous phase outlet of the dehydration flash tank (114) is connected with an inlet of a first-stage condenser (112), an outlet of the first-stage condenser (112) is respectively connected with a recovery system and an inlet of a second-stage condenser (113), an outlet of the second-stage condenser (113) is respectively connected with the recovery system and a vacuum unit, a liquid phase outlet of the dehydration flash tank (114) is connected with an inlet of a flash liquid pump (116), an outlet of the flash liquid pump (116) is connected with an inlet of a second-stage cooler (111), an acetone raw material pipeline is respectively connected with the inlet of the first-stage cooler (109) and the inlet of the second-stage cooler (111), and a phenol raw material pipeline is connected with the inlet of the first-stage cooler (109); an inlet of each reactor in a second-stage reaction system is connected with an outlet of the second-stage cooler (111), an outlet of each reactor is respectively connected with the inlet of the interstage preheater (110) and an inlet of an adsorption column, an outlet of a second-stage first-section reactor (105) is connected with an inlet of a second-stage second-section reactor (106), and an outlet of the second-stage second-section reactor (106) is connected with an inlet of a second-stage third-section reactor (107); an outlet of the second-stage third-section reactor (107) is connected with an inlet of a second-stage fourth-section reactor (108), and an outlet of the second-stage fourth-section reactor (108) is connected with an inlet of the second-stage first-section reactor (105); pipelines in each stage of reaction system are controlled to be connected or disconnected through valves, such that any three reactors can be connected in series; and an outlet of the adsorption column is connected with an inlet of a bisphenol A concentration system through a pipeline.

4. The device for the bisphenol A preparation process according to claim 3, wherein an outlet temperature on a cooling side of the first-stage cooler ranges from 65° C. to 70° C.; unit bed pressure drop of the first-stage reactors connected in series ranges from 15 kPa/m to 30 kPa/m; and outlet temperatures of the first-stage reactors connected in series are less than 76° C., and an outlet temperature of the first-stage circulating heat extraction pump ranges from 72° C. to 76° C.

5. The device for the bisphenol A preparation process according to claim 3, wherein an outlet temperature on a cooling side of the second-stage cooler ranges from 65° C. to 70° C.; a unit bed pressure drop of the second-stage reactors connected in series ranges from 7 kPa/m to 28 kPa/m; and outlet temperatures of the second-stage reactors connected in series range from 72° C. to 80° C.

6. The device for the bisphenol A preparation process according to claim 3, wherein an outlet temperature on a heating side of the interstage preheater ranges from 85° C. to 90° C.; and a pressure of the dehydration flash tank ranges from 3 kPaA to 7 kPaA.

7. The device for the bisphenol A preparation process according to claim 3, wherein a flow ratio of material flow from the outlets of the second-stage reaction system entering the interstage dehydration system to material flow fed onto the adsorption column ranges from 0.8:1 to 1:1.

* * * * *